United States Patent
Chornenky et al.

(10) Patent No.: US 7,338,487 B2
(45) Date of Patent: Mar. 4, 2008

(54) DEVICE FOR DELIVERING LOCALIZED X-RAY RADIATION AND METHOD OF MANUFACTURE

(75) Inventors: Victor I. Chornenky, Minnetonka, MN (US); Michael R. Forman, St. Paul, MN (US)

(73) Assignee: Medtronic Vascular, Inc., Santa Rosa, CA (US)

(*) Notice: Subject to any disclaimer, the term of this patent is extended or adjusted under 35 U.S.C. 154(b) by 431 days.

(21) Appl. No.: 10/010,911

(22) Filed: Nov. 20, 2001

(65) Prior Publication Data

US 2002/0146090 A1   Oct. 10, 2002

Related U.S. Application Data

(63) Continuation of application No. 09/123,669, filed on Jul. 28, 1998, now abandoned, which is a continuation of application No. 08/806,244, filed on Feb. 21, 1997, now Pat. No. 6,377,846, which is a continuation-in-part of application No. 08/701,764, filed on Aug. 22, 1996, now Pat. No. 6,799,075.

(60) Provisional application No. 60/006,708, filed on Nov. 14, 1995, provisional application No. 60/002,722, filed on Aug. 24, 1995.

(51) Int. Cl.
*A61B 18/18*   (2006.01)
*A61B 5/10*   (2006.01)

(52) U.S. Cl. .......................... 606/33; 604/20; 378/65

(58) Field of Classification Search ............... 606/32, 606/34; 378/91, 101, 119, 121, 122, 64, 378/65; 604/19, 20
See application file for complete search history.

(56) References Cited

U.S. PATENT DOCUMENTS

| | | | |
|---|---|---|---|
| 4,834,100 A | * | 5/1989 | Charms |
| 5,090,043 A | * | 2/1992 | Parker et al. .............. 378/65 |
| RE34,421 E | | 10/1993 | Parker et al. |
| 5,428,658 A | | 6/1995 | Oettinger et al. |
| 5,504,798 A | * | 4/1996 | Suzuki .................... 378/121 |

FOREIGN PATENT DOCUMENTS

| | | |
|---|---|---|
| EP | 0 633 041 B1 | 9/1999 |
| WO | WO95/19807 | 7/1995 |

* cited by examiner

*Primary Examiner*—David M. Shay

(57) ABSTRACT

Generally, the present invention provides a device for insertion into a body of a subject being treated to deliver localized x-ray radiation, and a method for fabricating such a device. The device includes a cathode structure that has a thin, diamond film as a cathode. The device further comprises a vacuum housing and an anode. A method for fabricating a device for localized x-ray radiation is described which includes the formation of a thin diamond film on a getter at temperatures below an activation temperature of the getter.

7 Claims, 2 Drawing Sheets

DEVICE FOR DELIVERING LOCALIZED X-RAY RADIATION AND METHOD OF MANUFACTURE

This patent application is a CONTINUATION of U.S. patent application Ser. No. 09/123,669, filed Jul. 28, 1998 abandoned, which is a CONTINUATION of U.S. patent application Ser. No. 08/806,244, filed Feb. 21, 1997 now U.S. Pat. No. 6,377,846 which is a CONTINUATION-IN-PART of U.S. patent application Ser. No. 08/701,764, filed Aug. 22, 1996, now U.S. Pat. No. 6,799,075 which claims benefit to U.S. Provisional application 60/006,708, filed Nov. 14, 1995, which claims benefit to U.S. Provisional application 60/002,722, filed Aug. 24, 1995, the entire contents of which are hereby incorporated by reference.

FIELD OF THE INVENTION

The present invention is directed to an x-ray device and method of fabrication, and more particularly to an x-ray device and method for fabrication for delivering localized radiation to vessels, lumens, or cavities of a body, such as cardiovascular tissue, to treat restenosis and other conditions.

BACKGROUND OF THE INVENTION

In the medical field, doctors and scientists strive to find less invasive ways to treat patients. By using treatments that are less intrusive to the body, doctors can greatly reduce the stress on the patient's systems and exposure to infection. For example, laparoscopic techniques enable physicians to explore the interior of the body and perform surgery through a small opening in the skin. Less intrusive medical techniques are extremely beneficial when applied to cardiovascular diseases.

Cardiovascular diseases affect millions of people, often causing heart attacks and death. One common aspect of many cardiovascular diseases is stenosis, or the thickening of the artery or vein, decreasing blood flow through the vessel. Angioplasty procedures have been developed to reopen clogged arteries without resorting to a bypass operation. However, in a large percentage of cases, arteries become occluded again after an angioplasty procedure. This recurrent thickening of the vessel is termed restenosis. Restenosis frequently requires a second angioplasty and eventual bypass surgery. Bypass surgery is very stressful on the patient, requiring the chest to be opened, and presents risks from infection, anesthesia, and heart failure.

Effective methods of preventing or treating restenosis could benefit millions of people. One approach uses drug therapy to prevent or minimize restenosis. For example, Heparin has been used as an anticoagulant and an inhibitor of arterial smooth muscle proliferation. Dexamethasone is another drug which may prevent smooth muscle proliferation. It has been suggested that such anticoagulants and antiproliferative agents may be effective at preventing restenosis after an angioplasty procedure thereby eliminating the necessity to repeat the procedure.

To be most effective and to reduce the associated risk, it is desirable to deliver such drugs directly to the region to be treated. In order to minimize the invasiveness of the procedure a drug delivery device that is adapted to traverse the human cardiovascular or circulatory system must be used. Such a device must be capable of entering small blood vessels with diameters of about two to four millimeters. Such a device must also be capable of making hairpin turns as it follows a tortuous path.

Many types of catheters have therefore been developed to deliver these and other effective drugs to the site of the restenosis. These catheters frequently use pressure to drive the drug into the tissue or plaque, potentially causing damage to the lumen wall. Techniques of delivery which do not use pressure use occlusion balloons to isolate the area from blood flow to enable sufficient absorption of the medication. However, the blood flow in an artery can only be occluded for a limited period of time while the drug is delivered. Due to these and other problems, localized delivery of drugs has not provided adequate treatment to prevent or reduce restenosis.

Another treatment for restenosis that has been attempted is beta-irradiation of the vessel wall by positioning radioactive isotopes in the vessel at the site of the restenosis. However, the depth of the penetration of the radiation is impossible to control with this method. The depth of the radiation is determined by the type of the radio-isotope used. The radioactive source will also irradiate other healthy parts of the body as it is brought to the site to be treated. Another disadvantage is that medical personnel must take extensive precautions when handling the radioactive material.

Thus, there is a need for effective methods and devices to treat the interior of the body with minimal intrusion. Effective, less invasive techniques for preventing and treating stenosis and restenosis at a lumen wall are especially needed.

SUMMARY OF THE INVENTION

Generally, the present invention provides a device to deliver localized x-ray radiation, and a method for fabricating such a device. In one particular embodiment of the invention, the device includes a cathode structure that has a thin, diamond film. The device further comprises an anode disposed within the vacuum housing, the diamond film being operative with the anode to produce localized x-ray radiation.

In alternate embodiments, the device may further include a connector or a shaft, connected to the vacuum housing.

In another particular embodiment of the invention, a device to deliver localized x-ray radiation includes a cathode structure comprising a thin, diamond film on a getter. This device further comprises an anode disposed within a vacuum housing, the diamond film being operative with the anode to generate localized radiation.

In another particular embodiment of the invention, a method for fabricating a device for localized x-ray radiation is described which includes the formation of a thin diamond film on a shaped getter using a laser ion source. The method includes the steps of providing a getter with a shaped surface, where the getter has an activation temperature, and forming a thin diamond film cathode on the getter at temperatures below the activation temperature. The method further comprises disposing the cathode in a vacuum housing and increasing the temperature to the activation temperature of the getter.

In another particular embodiment of the invention, a transmissive device for insertion into the body of a patient is disclosed including a catheter and a flexible coaxial cable that is capable of conducting a voltage of greater than or equal to 10 kilovolts without electrical discharge.

In another particular embodiment of the invention, a method for conducting current in a body is disclosed, using the transmissive device of this invention.

In another particular embodiment of this invention, a device for insertion into a body includes a connector and a composite structure of boron nitride that joins a cathode and an anode.

BRIEF DESCRIPTION OF THE DRAWINGS

The invention may be more completely understood in consideration of the detailed description of various embodiments of the invention which follows in connection with the accompanying drawings, in which.

Figure 1:
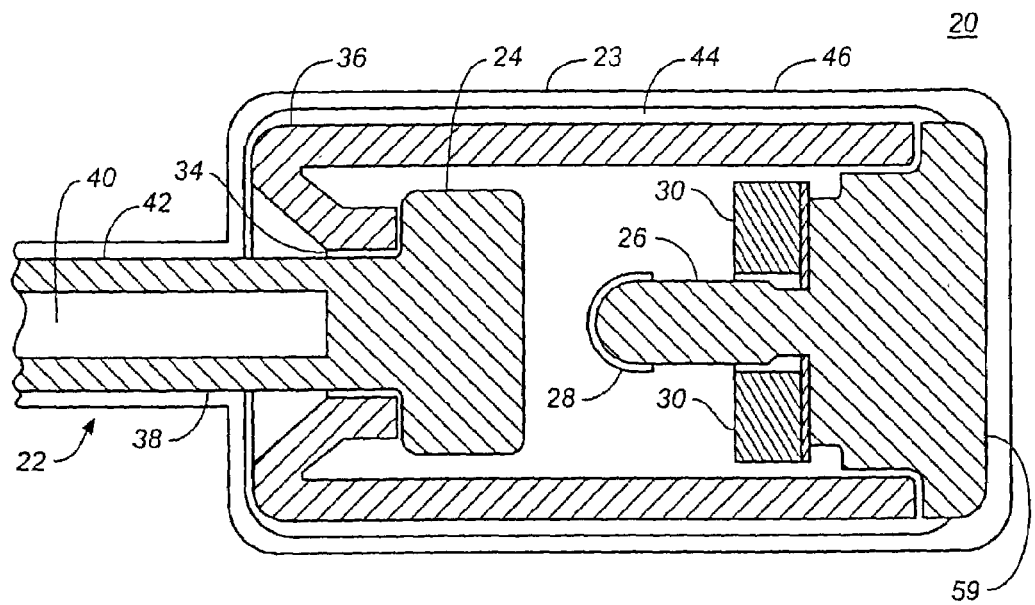
FIG. 1 shows an exploded cross-sectional view of an embodiment of the x-ray device of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the invention is to cover all modifications, equivalents, and alternatives falling within the spirit and scope of the invention as defined by the appended claims.

DETAILED DESCRIPTION OF THE VARIOUS EMBODIMENTS

The present invention is applicable to a variety of devices, methods of fabrication, methods of use, systems and arrangements which irradiate lumens, vessels, or interior sites in a body with x-ray radiation. The invention is particularly advantageous in preventing restenosis in the cardiovascular system. While the present invention is not so limited, an appreciation of various aspects of the invention is best gained through a discussion of application examples operating in such an environment.

FIG. 1 illustrates a first embodiment in which a cathode of an x-ray device 20 comprises a thin diamond film 28 which may be used to deliver localized x-ray radiation to treat, for example, restenosis. In coronary applications, it is desirable to have the x-ray radiation penetrate into the adventitia tissue of the blood-vessel about 2 millimeters deep. Penetration into the cardiac muscle tissue should be minimized. It is further desirable to deliver x-ray radiation with a peak energy of about 8–10 kiloelectronvolts (keV) in coronary applications.

While attempting to produce x-ray radiation of about 8–10 keV in the body, it is important to keep the magnitude of the electrical field at the surface of the cathode as low as possible. An electrical field exists at the surface of the cathode 26, while just on the outside of the vacuum housing a conductive braid or solder 44 is held at ground. An electrical discharge from the surface of the cathode to ground, or an electric flashover, must be prevented. According to the present invention, as a weaker electrical field is required by the x-ray source, the danger of electrical flashover is reduced, less heat is generated, and a wider array of conductors can be used.

In addition, the ability to lower the required electric field at the cathode results in a less expensive manufacturing technique. Small irregularities on the surface of the cathode result in an increase in the magnitude of the electrical field for an applied voltage, thereby increasing the chance of electrical flashover. The weaker the required electrical field at the cathode, the more imperfections can be tolerated on the cathode surface without risking flashover.

In accordance with one embodiment of the invention x-ray radiation is produced, while keeping the required electrical field low, by using a diamond film as a cathode. Diamond coatings display attractive properties as field emitters, losing electrons easily as a field is applied. Where a diamond coating is used as the cathode, the electrical field required to produce about 8–10 keV of radiation is about 20 keV/micron. In contrast, the required electrical field to produce a similar level of radiation from a metal emitter is well over 1,000 keV/micron. In the present invention, a diamond-coated cathode is used to achieve x-ray treatment radiation while producing significantly weaker electrical fields at the cathode.

X-ray devices for use inside a body are discussed in co-pending U.S. application Ser. No. 08/701,764, filed Aug. 24, 1996, the entire contents of which are incorporated herein by reference.

Now referring to FIG. 1, in this embodiment, the x-ray device 20, or transmissive device 20, comprises a flexible catheter shaft 22 adapted for insertion into blood vessels, lumens, or other body cavities. While in this particular embodiment a catheter shaft is shown, generally, many different elements could be used to guide the x-ray device of the present invention to a treatment site. The shaft 22 or connector has a proximal and distal portion, the distal portion being shown in FIG. 1. In coronary applications, the device may be inserted in the body at the femoral artery and threaded through a network of blood vessels to reach the heart. In this context the shaft or connector must be extremely flexible and have a maximum diameter less than or equal to about 3 millimeters. In other applications, the properties of the shaft must meet the requirements of the task.

At the distal portion of the flexible shaft 22, a composite structure is coupled. The composite structure includes a vacuum housing 23 is provided, which encloses the x-ray source components. The x-ray source components include an anode 24, a cathode base 26, a thin diamond film 28 located on the cathode base 26, and a getter 30. The outer diameter of the integrated x-ray device shown in FIG. 1 is less than or equal to approximately 2.5 millimeters.

In order to apply an electric field across the anode and cathode, a coaxial cable 38 may be disposed within the shaft 22. In this embodiment, the coaxial cable 38 is coupled to a high voltage generator, not shown, at the proximal end of the shaft 22. An internal conductor 40 of the coaxial cable 38 is coupled to the anode 24 at the appropriate voltage. An external conductive layer 42 of the coaxial cable 38 is held at ground and coupled to the cathode base 26 via a conductive solder 44. Other known methods may also be used to apply the electric field across the anode and cathode.

A coronary artery after dilatation by angioplasty typically has a diameter of only about 3.0 millimeters. Therefore, a coaxial cable and any covering used in this device must have a diameter of less than or equal to 3.0 millimeter. The cable must also be able to carry the required voltages and have sufficient flexibility to make numerous sharp turns as it follows the artery path. Standard high voltage coaxial cables are generally not flexible enough. However, the inventors have found that miniature high frequency coaxial cables with an outer diameter of approximately 1.0 millimeter to 3.0 millimeters are available which also exhibit sufficient flexibility. These types of cables are typically used in high frequency applications at voltages less than several kilovolts (kV). In connection with the present invention, the inventors have discovered that such cables can hold direct current voltages as high as 75–100 kV without breakdown. Therefore, these cables are well suited for use with the x-ray device of the present invention. In one embodiment, a cable with an outer diameter less than or equal to 3.0 millimeters is used. In another embodiment, the cable has an outer diameter of 1–2 millimeters. Such cables are manufactured by, for example, New England Electric Wire Corporation, Lisborn, N.H.

In order to most effectively decelerate the electrons striking the anode, a heavy metal material can be used for the anode 24, such as tungsten or gold. The material used for the cathode base 26 depends on how the diamond film is formed. The thin diamond film 28 can be obtained by chemical vapor deposition, as is known in the art. Various materials may serve as an effective substrate for diamond film synthesis by chemical vapor deposition, such as tungsten, molybdenum, and tantalum. As described more fully below, the diamond film could also be fabricated by other methods, such as by laser ion deposition, making a wider range of materials available for the base of the cathode.

The term diamond film, as used herein, contemplates a coating of carbon having diamond-like bonds which demonstrate negative electron affinity. It is also desirable to have sufficient conductivity to create a constant supply of electrons to the surface of the cathode. The presence of some graphite bonds in the diamond film will contribute to conductivity. Thus a combination of a diamond film having both sp3 carbon bonds, to function as a cathode, and some sp2 carbon bonds, to facilitate conductivity, is particularly suited for use in such a system. Other elements may also be present in the film in small quantities. According to the invention, the diamond film will have the property that it can emit electrons at electrical fields greater than or equal to about 20 keV/micron. This required electric field is extremely low when compared to that required for metal emitters such as molybdenum or silicon, which require greater than 1,000 keV/micron.

A getter 30 is disposed within the vacuum housing 23 in order to aid in creating and maintaining a vacuum condition of high quality. The getter 30 has an activation temperature, at which it will react with stray gas molecules in the vacuum. After the getter 30 is disposed within the vacuum housing and the housing pumped out, the device is heated to the activation temperature. It is desirable that the getter used have an activation temperature that is not so high that the x-ray device will be damaged when heated to the activation temperature. A SAES ST 101 alloy getter could be used, which has an activation temperature in the range 750 to 900° C. and is composed of approximately 64% zirconium and 16% aluminum. A ST 707 alloy getter could also be used, which has an activation temperature in the range 400–500° C. and is composed of approximately 70% zirconium, 24.6% vanadium, and 5.4% iron.

A wall of the vacuum chamber 36 should be transparent to x-rays in order to allow the full dosage to reach the lumen wall. The wall 36 can comprise pyrolytic boron nitride, or another metal or ceramic material which is transparent to x-rays. Other possibilities include beryllium, beryllium oxide, aluminum, aluminum oxide, or graphite.

In the x-ray device an electrical field exists at the surface of the cathode 26 and current flows from the cathode 26 to the anode 24, while just on the outside of the vacuum housing a conductive braid or solder 44 is held at ground. In accordance with the present invention, these two potentials must be insulated from each other or electrical flashover will occur. A vacuum wall of pyrolytic boron nitride can provide some insulation. If a metal is used as the vacuum chamber wall 36, an insulative layer is necessary. As additional protection against electrical flashover, an electrically insulating material 50 can be placed at the joints of the vacuum chamber wall. The vacuum chamber further includes a biocompatible coating 46, such as polyethylene, polyurethane or Teflon®. The joints 34 between the vacuum chamber wall 36 and the anode 24 can be vacuum furnace brazed.

When used to radiate the wall of a lumen, according to one embodiment of the invention, the x-ray device is placed within a catheter. The catheter is introduced into the lumen to be treated through the skin. The x-ray device is then guided through the lumen, using techniques known in the art, until it is positioned near the area to be radiated.

The high voltage generator is activated and an electrical field is established across the cathode 28 and the anode 24. The thin diamond coating 28 loses electrons which are accelerated toward the anode 24. As the electrons are decelerated by the anode 24, electromagnetic radiation is emitted by the material of the anode 24. In this manner, x-ray radiation is produced by the Bremsstrahlung effect. As the x-ray radiation impinges upon the wall of the lumen, it inhibits smooth muscle proliferation. Thus, the x-ray catheter device can be used to effectively prevent restenosis. When the desired dosage has been delivered, the voltage source is discontinued and the catheter withdrawn from the body.

A certain amount of heat is generally generated by the x-ray unit at the anode. Thus, some mechanism for cooling the structure may be required. When used in an artery, the typical blood flow to an artery is about 50–60 cm$^3$/minute, which aids in dissipating heat conducted through the vacuum housing. Where the x-ray device is used in other body systems, additional cooling methods may be required.

Figure 2:
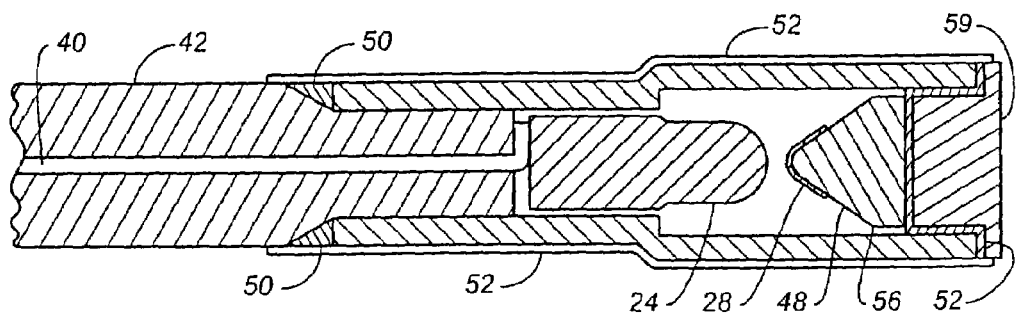
FIG. 2 shows an exploded cross-sectional view of another embodiment of the x-ray device of the present invention.

Now referring to FIG. 2, another embodiment of the x-ray device of the present invention is illustrated. In the embodiment of FIG. 2, a thin diamond film is placed directly on a getter. According to the invention, by incorporating the getter into the cathode structure, significant size advantages can be obtained.

Treatments for cardiovascular disease continue to become less invasive in the patient's body and therefore less stressful to the patient's system. Size improvements on an x-ray device could reduce the size of the required incision, improve maneuverability, decrease the stress on the lumen, and enable the device to reach more remote locations in the patient's body. By combining a cathode and a getter in an x-ray device, it is possible to eliminate components and permit a significant size reduction.

Laser ion source deposition may be used to place the diamond film directly upon a getter. A traditional chemical vapor deposition process takes place at approximately 900° C. Therefore, a getter used as a substrate in such a process would be activated and used up during the deposition process. However, the use of a laser ion source deposition process, which can be carried out at room temperature, allows a diamond film to be created on a getter without activating the getter. A laser ion source deposition process is described in U.S. Pat. No. 4,987,007, Wagal et al. U.S. Pat. No. 4,987,007, in its entirety is hereby incorporated by reference. The outer diameter of the integrated x-ray device of the embodiment illustrated in FIG. 2 will be less than or equal to approximately one and one quarter millimeters.

The outer vacuum housing features of FIG. 1 may also be used in the embodiment shown in FIG. 2, although these features are not illustrated in FIG. 2. For example, the outer biocompatible layer, vacuum furnace brazed joints and insulating material may be used in the embodiment of FIG. 2. In FIG. 2, a conductive solder material 52 provides an electrical connection between the external conductive layer 42 of the coaxial cable and the cathode base 48.

The getter 56 will be conductive enough to provide the electrical connection between the thin diamond film 28 and the conductive solder 52. The ST 707 alloy getter could also be used, which has an activation temperature in the range 400–500° C. and is composed of approximately 70% zirconium, 24.6% vanadium, and 5.4% iron.

Figure 3:
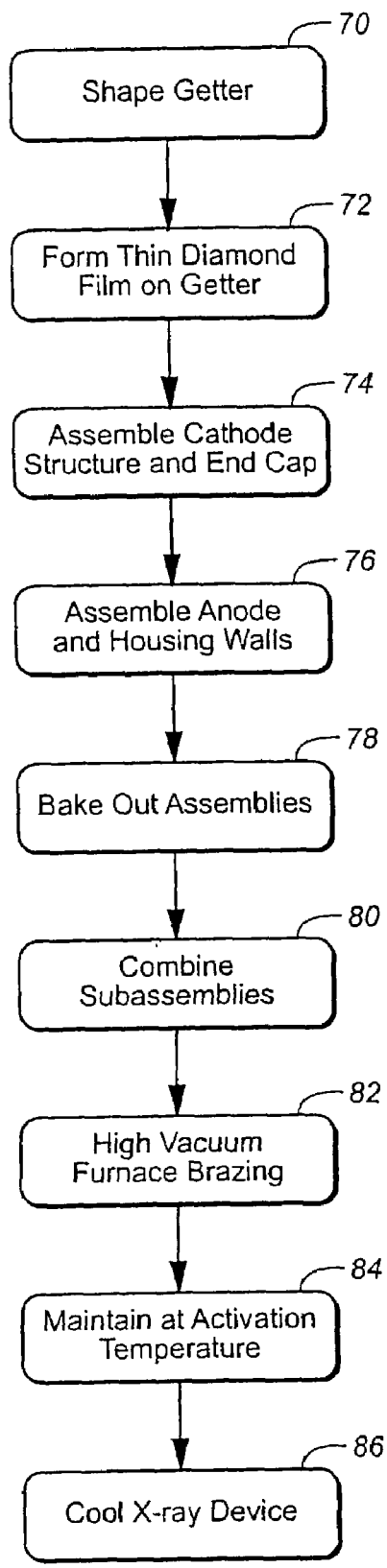
FIG. 3 illustrates the steps involved in a method of fabricating an x-ray device of the present invention.

FIG. 3 shows a method for creating the x-ray device of the second embodiment. First, the getter is machined into a desirable shape for the cathode in step 70. A cone shape or rounded cone shape, for example, may be used for the shape of the cathode. Next, a thin diamond film is formed on a tip-portion of the getter in step 72. The tip portion of the getter corresponds to a cathode structure. The diamond film formation is carried out at a temperature below the activation temperature of the getter using, for example, laser ion source deposition techniques. Two subassemblies are constructed. In step 74, one subassembly comprises the cathode structure and an end cap 59. The other subassembly of step 76 comprises the anode 24 and the vacuum chamber walls 36. These two subassemblies are sealed in a high vacuum furnace and heated to approximately 400–500° C. to bake out gas molecules from the materials for about two hours in step 78. The subassemblies are sealed together in step 80, while still at high vacuum furnace conditions. The temperature is increased to approximately 500–700° C. for step 82 high vacuum furnace brazing of the joints of the x-ray device. The device is maintained at a high temperature for several hours to thoroughly activate the getter in step 84. The device is cooled in step 86, tested, and cables are attached.

In the device of this method, the getter is a miniature vacuum pump disposed within the vacuum housing. This method permits the manufacture of an x-ray device having an outer diameter of less than or equal to approximately one and one-quarter millimeter.

The various embodiments described above are provided by way of illustration only and should not be construed to limit the invention. Those skilled in the art will readily recognize various modifications and changes which may be made to the present invention without strictly following the exemplary embodiments and applications illustrated and described herein, and without departing from the true spirit and scope of the present invention which is set forth in the following claims.

We claim:

1. A transmissive device for insertion into a patient's cardiovascular system, comprising:
   a catheter with a lumen, the catheter having a proximal portion and a distal portion;
   an x-ray source at the catheter distal portion, the x-ray source having a vacuum chamber defined by a chamber wall and containing an anode and cathode for generating an electrical field, the vacuum chamber having a diameter less than 3 mm;
   an electrically insulating material positioned between the vacuum chamber wall and the anode at joints of the vacuum chamber wall;
   a flexible coaxial cable in the lumen having a center conductor coupled to the anode and an external conductor; and
   a conductive layer overlying a portion of the vacuum chamber coupling the cathode to the external conductor of the flexible coaxial cable.

2. The device of claim 1 further comprising a biocompatible coating over the flexible coaxial cable.

3. The device of claim 1 wherein an electric field of approximately 20 keV/micron or less is applied across the anode and cathode to generate x-ray radiation.

4. The device of claim 1 wherein the conductive layer is solder.

5. The device of claim 1 wherein the x-ray source generates radiation in a range of 8–10 keV.

6. The device of claim 1 wherein the device further includes a housing protecting the x-ray source.

7. The device of claim 6 wherein the housing is transmissive to x-rays and comprises boron nitride.

* * * * *